(12) United States Patent
Azar

(10) Patent No.: US 6,758,852 B1
(45) Date of Patent: Jul. 6, 2004

(54) CORNEAL FLAP SLICER

(75) Inventor: Dimitri T. Azar, Brookline, MA (US)

(73) Assignee: Massachusetts Eye & Ear Infirmary, Boston, MA (US)

(*) Notice: Subject to any disclaimer, the term of this patent is extended or adjusted under 35 U.S.C. 154(b) by 0 days.

(21) Appl. No.: 10/299,966

(22) Filed: Nov. 19, 2002

(51) Int. Cl.[7] .................................................. A61F 9/00
(52) U.S. Cl. .................................................... 606/166
(58) Field of Search ............................ 606/166, 170, 606/171, 177, 4–6

(56) References Cited

U.S. PATENT DOCUMENTS 4,173,980 A * 11/1979 Curtin ........................ 606/166
6,527,788 B1 * 3/2003 Hellenkamp ................ 606/166
6,596,006 B1 * 7/2003 Hanna ........................ 606/166
6,599,305 B1 * 7/2003 Feingold .................... 606/166
2003/0018348 A1 * 1/2003 Pallikaris et al. ........... 606/166

* cited by examiner

Primary Examiner—(Jackie) Tan-Uyen T. Ho
(74) Attorney, Agent, or Firm—Fish & Richardson P.C.

(57) ABSTRACT

An apparatus for forming a corneal flap includes a housing from which extend a shaft and a reciprocating member. An aplanating member is mounted at a distal end of the shaft to aplanate a region of the cornea. A cutting blade is mounted to the reciprocating member at a position selected to slice the aplanated region off the cornea.

8 Claims, 3 Drawing Sheets

CORNEAL FLAP SLICER

FIELD OF INVENTION

This invention relates to ophthalmic surgery, and in particular, to surgery on the cornea.

BACKGROUND

The cornea of the eye plays a role in focusing light. By changing the shape of the cornea, it is possible to correct a patient's vision. Common surgical procedures for changing the shape of the cornea include temporarily removing the epithelium of the cornea to expose the underlying stroma, ablating selected portions of the stroma with a laser, and replacing the epithelium over the stroma.

In LASEK ("Laser assisted Sub Epithelial Keratomilieusis") surgery, an incision along a circular arc on the cornea is made and the resulting flap is pulled back to expose the stroma of the cornea. The flap includes the epithelium and the Bowman's membrane separating the epithelium from the stroma. Unlike the flap that is made during LASIK ("Laser assisted In situ Keratomilieusis"), this flap does not include any portion of the stroma. Thus, when the flap is pulled back, it is the surface of the stroma, and not the interior of the stroma, that is exposed to the laser. This procedure thus results in a lower risk of complications.

In practice, because the epithelium is so thin, it is difficult to cut a flap without also cutting into the stroma.

SUMMARY

In one aspect, the invention includes an apparatus for forming a corneal flap. The apparatus includes a housing from which a shaft and a reciprocating member extend. At the distal end of the shaft is mounted an aplanating member for aplanating a region of the cornea. At the distal end of the reciprocating member is mounted a cutting blade for slicing an aplanated region of the cornea.

In some embodiments, the aplanating member is a roller, while in other embodiments, the aplanating member is a runner.

The cutting blade can be a wire, a knife, or any other structure configured to slice into the cornea.

In some embodiments, the aplanating member and the cutting blade are offset by an amount corresponding to a desired thickness of the flap. The aplanatihg member can be offset from the cutting member in either the proximal or distal direction.

Another aspect of the invention is an apparatus in which a forked end of a shaft defines a gap. An aplanating member, for aplanating a region of the cornea, extends across this gap. The apparatus also includes a reciprocating member having a distal tip formed into a bow. A cutting blade extends across this bow and is disposed to slice the aplanated region off the cornea.

In another aspect, the invention provides a method for forming a corneal flap by aplanating a region of the cornea and placing a reciprocating cutting blade on the aplanated region. The flap is then formed by translating the cutting blade across the aplanated region.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

These and other features and advantages of the invention will be apparent from the following detailed description and the accompanying figures, in which:

DETAILED DESCRIPTION

Figure 1:
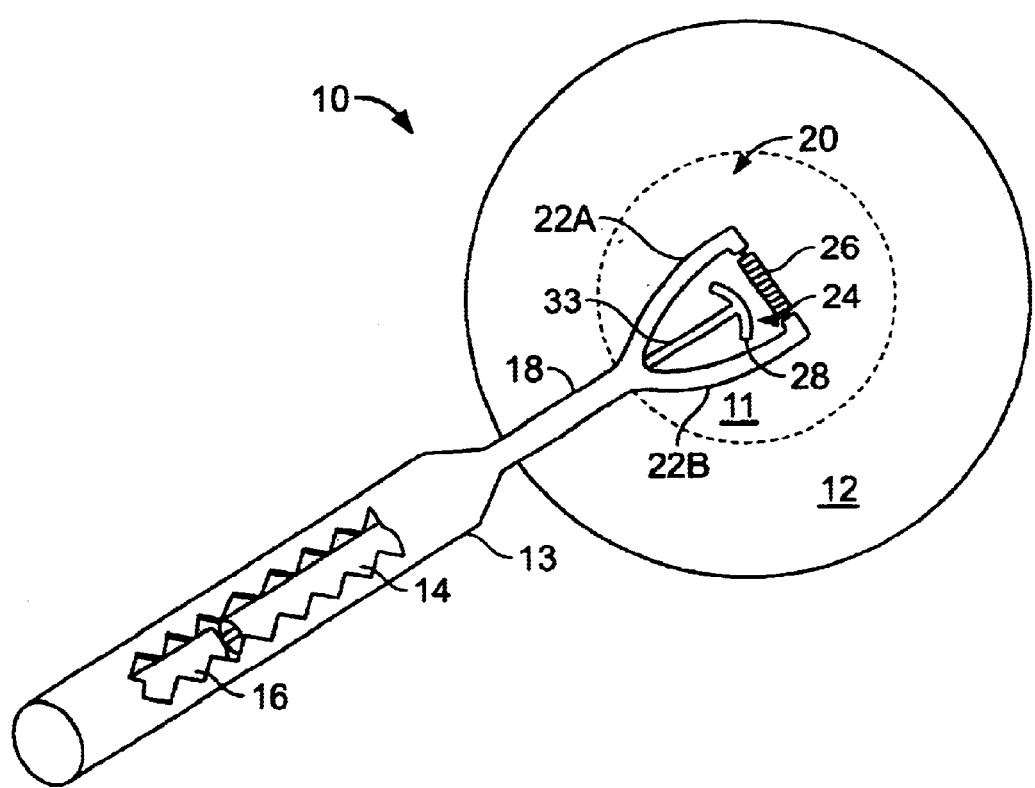
FIG. 1 shows a surgical instrument incorporating the invention.

Referring to FIG. 1, a surgical instrument 10 for cutting a flap 11 in the cornea 12 includes a housing 13 that encloses a motor 14. Also within the housing 13 is a power supply 16, such as a battery, for providing power to the reciprocating motor 14. A stationary shaft 18 extends distally from the housing 13 to a cutting tip 20 disposed at a distal end thereof.

Figure 2:
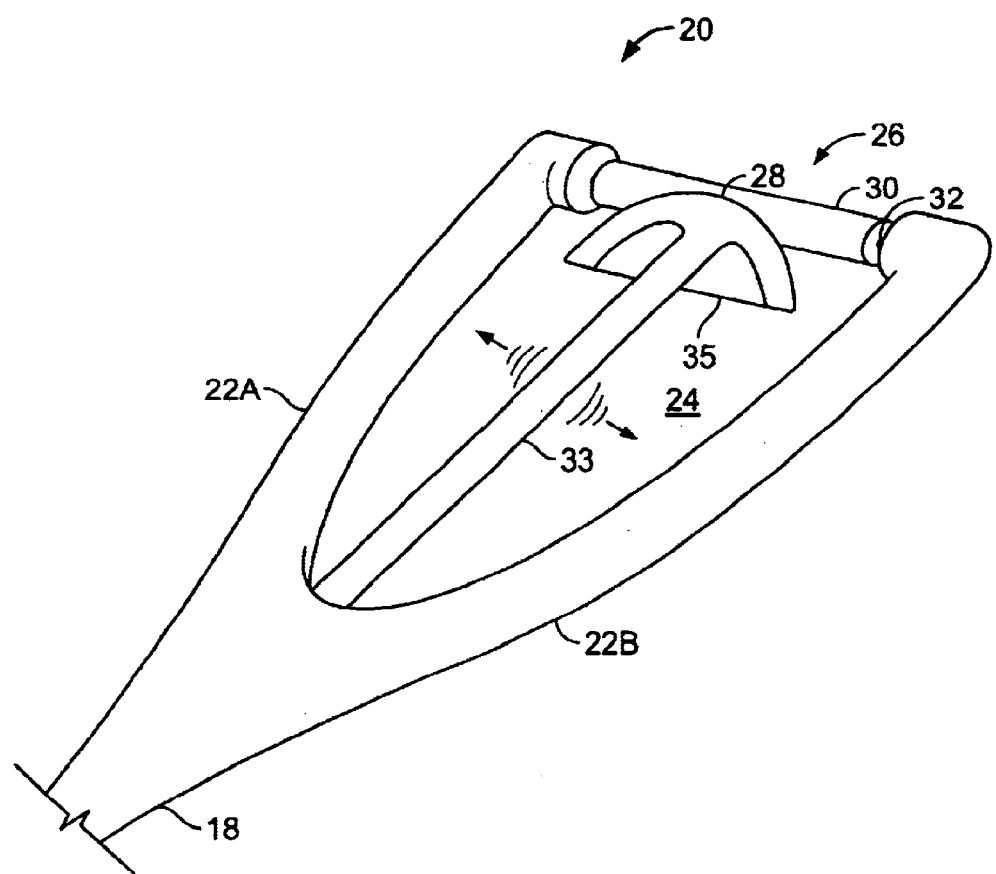
FIG. 2 shows the distal tip of the surgical instrument shown in FIG. 1.

At its distal end, the shaft 18 bifurcates into two prongs 22A–B separated by a gap 24. An aplanating member 26, best seen in FIG. 2. extends between the prongs 22A–B and across the gap 24. In the illustrated embodiment, the aplanating member 26 includes a roller 30 mounted to rotate about an axle 32 that extends across the gap 24. The coupling between the roller 30 and the axle 32 has a coefficient of rolling friction that is low enough to enable it to roll as it is dragged across the cornea 12. The aplanating member 26 can also be a stationary rod or runner having a cross section that includes a curved contact surface for sliding across the cornea 12. The aplanating member 26 is preferably made from a biocompatible material having a low coefficient of sliding friction.

The cutting tip 20 includes a bow 28 mounted at the distal tip of a reciprocating member 33. The motor 14 is coupled to the reciprocating member 33 so as to cause the bow 28 to move from side to side in a direction parallel or essentially parallel to the aplanating member 26. In some embodiments, the motor 14 is coupled so as to cause the bow 28 to undergo orbital motion by moving along an elliptical path having a major axis parallel to the aplanating member 26.

Figure 3:
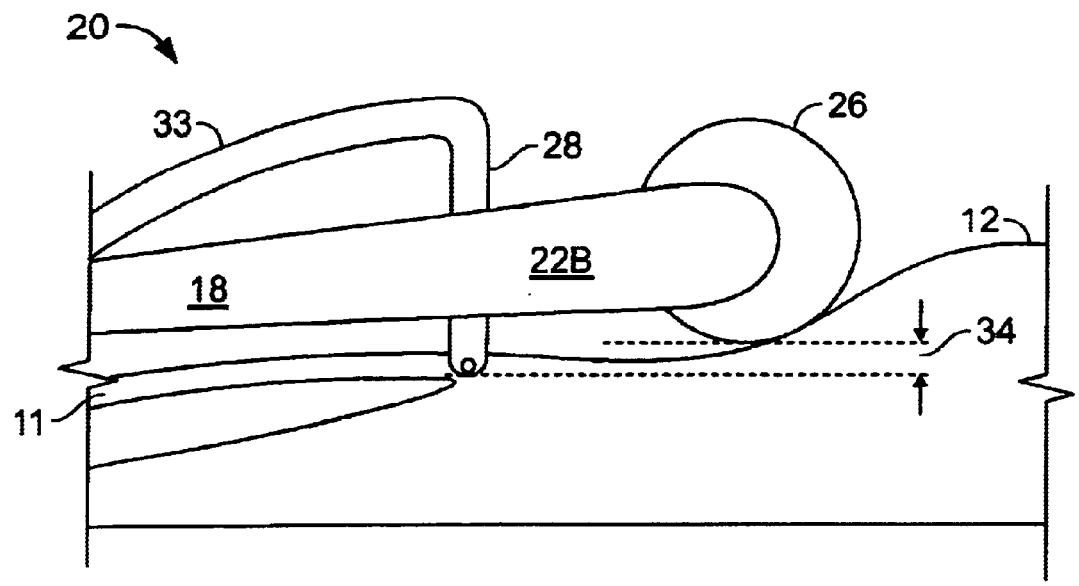
FIG. 3 shows the surgical instrument slicing into the cornea.

A cutting blade 35, which can be a wire or a knife, extends across the opening of the bow 28 in a direction parallel to the aplanating member 26. Referring to FIG. 3, the cutting blade 35 lies in a cutting plane that is vertically offset from a plane defined by the two prongs 22A–B. The extent of this vertical offset 34 controls the thickness of the flap 11. The cutting blade 35 is also horizontally offset from the aplanating member 26 either distally or proximally. The extent of this horizontal offset 36 is selected such that the surface of the cornea 12 that is exposed to the cutting blade 35 remains essentially flat even though it no longer lies under the aplanating member 26.

As shown in FIG. 3, the aplanating member 26 is placed on the cornea 12 to flatten the cornea 12 in a region exposed to the reciprocating cutting blade 35. The surgeon then translates the surgical instrument 10. In the case in which the cutting blade 35 lies proximal to the roller 30, the surgeon translates the surgical instrument 10 distally. Conversely, when the cutting blade 35 lies distal to the roller 30, the surgeon translates the surgical instrument 10 proximally. In either case, the direction of motion is selected so that the cutting blade 35 slices into a portion of the cornea 12 that has recently been flattened, or aplanated, by the aplanating member 26.

Figure 4:
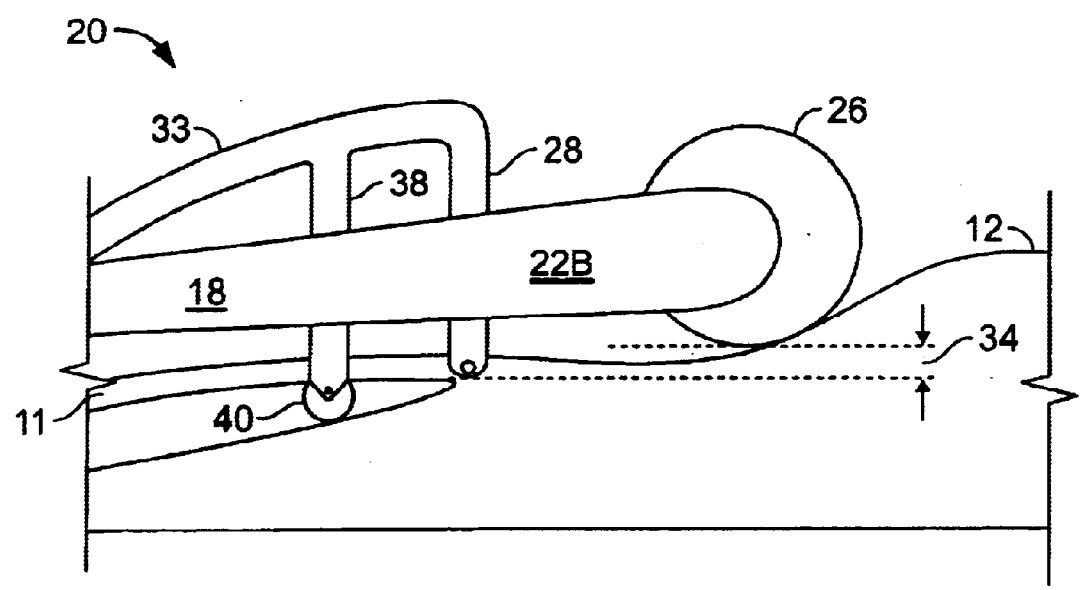
FIG. 4 shows an alternative embodiment of the surgical instrument.

In another embodiment, shown in FIG. 4, an additional bow 38 is mounted onto or integrally formed with the reciprocating member 33 proximal to the cutting blade 35. A lifting rod 40 extends across the additional bow 38 to support the flap that is sliced by the cutting blade 35. Because the lifting rod 40 reciprocates with the reciprocating member 33, the flap is unlikely to adhere to the lifting rod 40 during surgery.

Using a surgical instrument 10 as described herein, a surgeon can rapidly slice a flap 11 having a uniform and pre-defined thickness. By appropriately selecting the vertical offset 34 between the cutting blade 35 and the aplanating member 26, the flap 11 can be sliced thinly enough to avoid exposing the stroma.

Having described the invention, and a preferred embodiment thereof, what I claim as new, and secured by Letters Patent is:

1. An apparatus for forming a corneal flap, the apparatus comprising:

a shaft having a forked end defining a gap;

an aplanating member extending across the gap for aplanating a region of the cornea;

a reciprocating member having a first bow formed on a distal tip thereof; and a cutting blade extending across the first bow and disposed to slice an aplanated region off the cornea.

2. The apparatus of claim 1, wherein the reciprocating member comprises a second bow formed proximal to the distal tip, the second bow defining a gap across which extends a lifting member disposed to suspend the sliced aplanated region from the cornea.

3. The apparatus of claim 1, wherein the aplanating member comprises:

an axle extending across the gap; and a roller mounted on the axle.

4. The apparatus of claim 1, wherein the aplanating member comprises a runner extending across the gap.

5. The apparatus of claim 1, wherein the cutting blade is selected from a group consisting of a wire and a knife.

6. The apparatus of claim 1, wherein the cutting blade is offset from the aplanating member by an amount corresponding to a desired thickness of the flap.

7. The apparatus of claim 1, wherein the cutting blade is proximal to the aplanating member.

8. The apparatus of claim 1, wherein the cutting blade is distal to the aplanating member.

* * * * *